(12) United States Patent
Todo et al.

(10) Patent No.: US 11,302,945 B2
(45) Date of Patent: Apr. 12, 2022

(54) COMMUNITY SYSTEM

(71) Applicant: TOYOTA JIDOSHA KABUSHIKI KAISHA, Toyota (JP)

(72) Inventors: Tetsu Todo, Aichi-ken (JP); Koichi Ikemoto, Nagoya (JP); Motoki Hamazaki, Toyota (JP); Katsuhiko Hirose, Toyota (JP); Atsushi Mizutani, Toyota (JP); Shuntaro Kato, Nagoya (JP); Yohei Tanigawa, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 357 days.

(21) Appl. No.: 16/568,632

(22) Filed: Sep. 12, 2019

(65) Prior Publication Data

US 2020/0099074 A1 Mar. 26, 2020

(30) Foreign Application Priority Data

Sep. 20, 2018 (JP) .............................. JP2018-175593

(51) Int. Cl.
| | |
|---|---|
| *H01M 8/0606* | (2016.01) |
| *C01B 3/04* | (2006.01) |
| *A61K 33/00* | (2006.01) |
| *A23L 3/3445* | (2006.01) |

(52) U.S. Cl.
CPC ........... *H01M 8/0606* (2013.01); *A61K 33/00* (2013.01); *C01B 3/047* (2013.01); *A23L 3/3445* (2013.01); *H01M 2220/10* (2013.01)

(58) Field of Classification Search
CPC .......... H01M 8/0606; H01M 2220/10; H01M 2250/10; A61K 33/00; C01B 3/047; A23L 3/3445; Y02B 10/10; Y02B 90/10; Y02E 60/10; Y02E 60/36; Y02E 10/50; Y02E 60/50; Y02P 20/129; Y02P 80/20
See application file for complete search history.

(56) References Cited

U.S. PATENT DOCUMENTS

| 2001/0025670 A1* | 10/2001 | Ovshinsky | ............ | C01B 3/0057 |
| | | | | 141/231 |
| 2004/0131901 A1* | 7/2004 | Yamashita | ........ | H01M 8/04216 |
| | | | | 48/174 |

FOREIGN PATENT DOCUMENTS

| JP | 2013-074760 A | 4/2013 |
| JP | 2014028985 A | 2/2014 |
| JP | 2016208694 A | 12/2016 |

* cited by examiner

*Primary Examiner* — Daniel Cavallari
(74) *Attorney, Agent, or Firm* — Dickinson Wright, PLLC

(57) ABSTRACT

The community system includes a hydrogen source, a hydrogen storage, an FC power generating facility, a hydrogen filler, a house group that uses electric power supplied from the FC power generating facility and hydrogen supplied from at least one of the hydrogen source and the hydrogen storage, and a management system that manages hydrogen in the community system. The hydrogen source is a hydrogen producing device that produces hydrogen using waste heat generated in a commercial and industrial installation or produces hydrogen from by-product gas produced in the commercial and industrial installation.

2 Claims, 7 Drawing Sheets

Fig.4

HYDROGEN MANAGEMENT DATABASE HMD

| RECORD | HOUSE ID | CURRENT HYDROGEN RESIDUAL AMOUNT V1[L] | LAST-MONTH-END HYDROGEN RESIDUAL AMOUNT V2[L] | HYDROGEN PRODUCTION AMOUNT V3[L] | HYDROGEN CONSUMPTION AMOUNT V4[L] | HYDROGEN PURCHASE AMOUNT V5[L] | HYDROGEN SALE AMOUNT V6[L] |
|---|---|---|---|---|---|---|---|
| 1 | HH011 | 30.2 | 12.5 | 2.1 | 4.4 | 20.0 | 0.0 |
| 2 | HH012 | 27.5 | 14.4 | 2.1 | 4.0 | 15.0 | 0.0 |
| 3 | HH013 | 21.6 | 13.0 | 2.1 | 3.5 | 10.0 | 0.0 |
| 4 | HH014 | 6.2 | 16.1 | 2.1 | 2.0 | 0.0 | 10.0 |
| 5 | HH021 | 17.5 | 8.5 | 2.3 | 3.3 | 10.0 | 0.0 |
| 6 | HH022 | 19.9 | 9.6 | 2.3 | 2.0 | 10.0 | 0.0 |
| 7 | HH023 | 3.7 | 13.2 | 2.3 | 1.8 | 0.0 | 10.0 |
| ... | ... | ... | ... | ... | ... | ... | ... |

V1=V2+V3−V4+V5−V6

COMMUNITY SYSTEM

CROSS REFERENCE TO RELATED APPLICATIONS

The present application claims the priority based on Japanese Patent Application No. 2018-175593 filed on Sep. 20, 2018, the disclosure of which is hereby incorporated by reference in its entirety.

BACKGROUND

Field

The present disclosure relates to a community system that uses hydrogen.

Related Art

Japanese Patent Application Publication No. 2013-74760 discloses a community system that supplies a house group with electric power using a fuel cell.

Meanwhile, a community system allowing efficient use of hydrogen has conventionally been desired.

SUMMARY

According to one aspect of the present disclosure, a community system that uses hydrogen is provided. The community system comprises: a hydrogen source; a hydrogen storage storing hydrogen supplied from the hydrogen source; an FC power generating facility with a fuel cell that generates electric power using hydrogen supplied from at least one of the hydrogen source and the hydrogen storage; a hydrogen filler that fills a fuel cell vehicle with hydrogen supplied from at least one of the hydrogen source and the hydrogen storage; a house group with multiple houses that use electric power supplied from the FC power generating facility and hydrogen supplied from at least one of the hydrogen source and the hydrogen storage; and a management system that manages hydrogen in the community system. The hydrogen source is a hydrogen producing device that produces hydrogen using waste heat generated in a commercial and industrial installation or produces hydrogen from by-product gas produced in the commercial and industrial installation.

BRIEF DESCRIPTION OF DRAWINGS

FIG. 4 is an explanatory view showing an example of a hydrogen management database;

DETAILED DESCRIPTION

Figure 1:
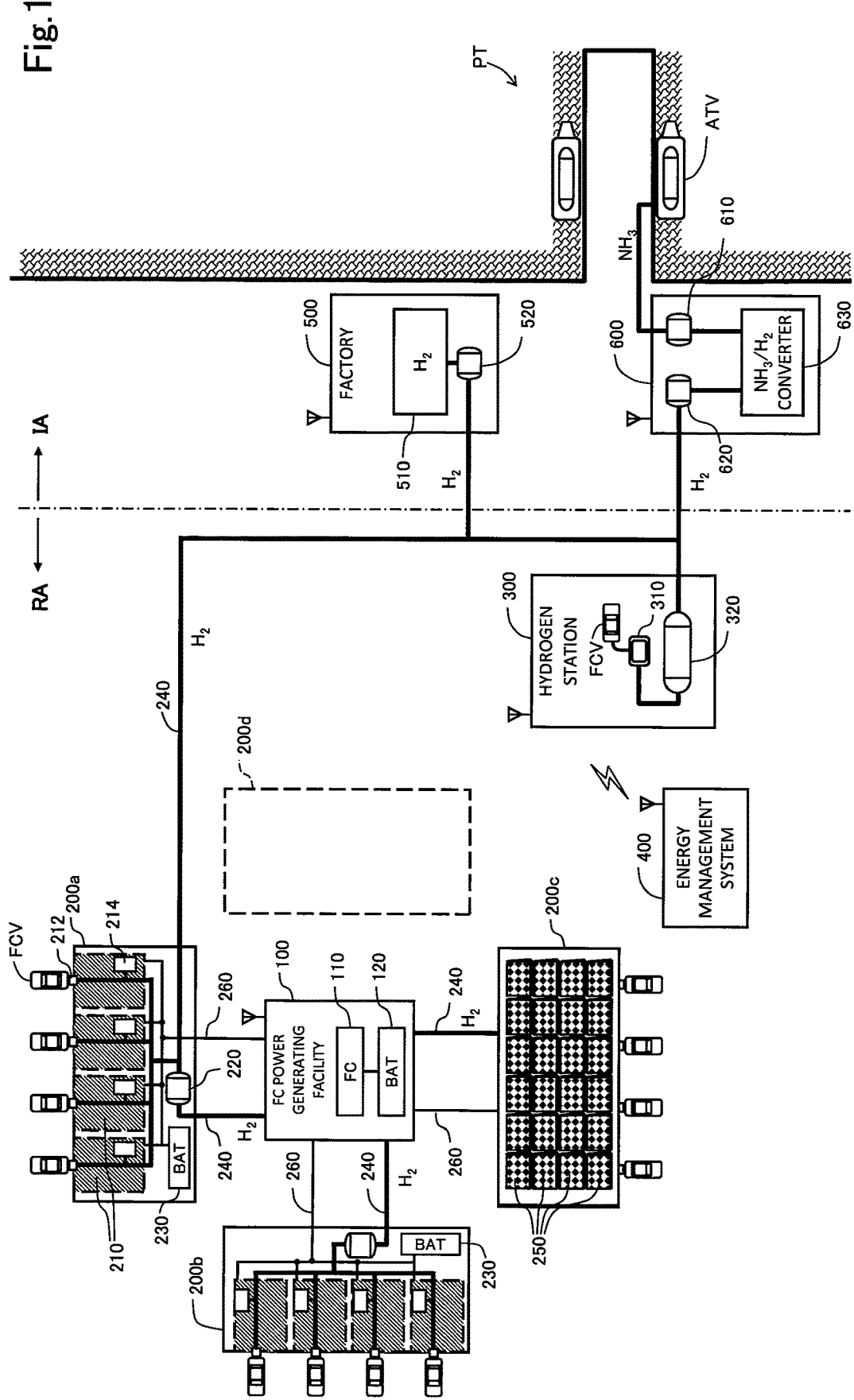
FIG. 1 is an explanatory view showing the configuration of a community system according to an embodiment.

FIG. 1 is an explanatory view showing the configuration of a community system according to an embodiment. This community system includes an FC power generating facility 100, a house group 200a, a house group 200b, a house group 200c, a house group 200d, a hydrogen station 300, an energy management system 400, a factory 500 with a hydrogen producing device, and an ammonia-hydrogen converting facility 600. The factory 500 and the ammonia-hydrogen converting facility 600 are located in an industrial area IA. The other facilities are located in a residential area RA. The residential area RA and the industrial area IA are use districts designated by a country or a municipality. This community system constructs a community that uses hydrogen efficiently, and hence it may also be called a "hydrogen community," a "hydrogen using community," or a "hydrogen smart community."

The FC power generating facility 100 includes a fuel cell system 110 and a secondary cell 120. The FC power generating facility 100 generates electric power with the fuel cell system 110 using hydrogen and supplies the generated electric power to the outside. Further, the FC power generating facility 100 accumulates redundant electric power in the secondary cell 120. The fuel cell system 110 is also simply called a "fuel cell."

Each of the four house groups 200a to 200d shown in FIG. 1 is one housing complex. The fourth house group 200d is yet to be built and a planned site for the house group 200d is indicated by dashed lines. Regarding two house groups 200a and 200b out of the three existing house groups 200a to 200c, inner residential zones are illustrated. Regarding the remaining one house group 200c, multiple roof-top solar panels 250 are illustrated. The solar panels 250 are also installable on wall surfaces or windows. In the following description, the house groups 200a to 200d will be called a "house group 200" collectively where the house groups 200a to 200d are not required to be distinguished from each other. Each house group 200 includes multiple houses 210, a hydrogen tank 220 as a hydrogen storage, and a secondary cell 230. In this embodiment, each house 210 is an apartment. Each house 210 is provided with a fuel cell vehicle FCV as a standard facility. Each house 210 is provided with a hydrogen supply nozzle 212 for filling the fuel cell vehicle FCV with hydrogen, and a hydrogen using facility 214 that uses hydrogen. The hydrogen supply nozzle 212 may be provided to each house 210. Alternatively, one or more hydrogen supply nozzles 212 common to one house group 200 may be provided. The hydrogen supply nozzle 212 is one type of hydrogen filler for filling the fuel cell vehicle FCV with hydrogen.

The following appliances are applicable as the hydrogen using facility 214, for example.

(1) A kitchen appliance that uses hydrogen gas.

(2) A hydrogen suction appliance used by a human for suction of hydrogen gas.

(3) A hydrogen water using appliance that uses hydrogen water.

The kitchen appliance that uses hydrogen may be a hydrogen grill for cooking using hydrogen gas or a refrigerator in which the freshness of vegetables is maintained with hydrogen gas supplied to a vegetable compartment, for example. The hydrogen grill is a cooking appliance for roasting food materials by combusting hydrogen gas. By the use of the hydrogen grill, steam wraps around food materials to roast the food materials with the steam. As a result, the food materials are roasted with heat quickly to allow cooking of the food materials without letting moisture or flavors in the food materials get away. By doing so, it becomes possible to maintain the textures or flavors of the food materials as they are. The refrigerator that uses hydrogen gas makes use of the properties of hydrogen of achieving an anti-oxidation effect that reduces active oxygen when hydrogen is used in the form of hydrogen gas. More specifically, the oxidation of vegetables is suppressed to maintain freshness by spraying hydrogen gas on the vegetables.

The hydrogen suction appliance used by a human for suction of hydrogen gas also makes use of the anti-oxidation effect of hydrogen. More specifically, when hydrogen gas is sucked into a human, active oxygen in the body of the human is reduced. Active oxygen is known to have a strong oxidizing effect that oxidizes and damages DNA, causing arterial sclerosis, muscle weakness, or aging. Suction of hydrogen gas into a human allows reduction in the occurrences of such types of degradation.

The hydrogen water using appliance that uses hydrogen water may be a hydrogen water dispenser for generation and supply of hydrogen water for drinking, a hydrogen bath, or a refrigerator in which the freshness of vegetables is maintained with hydrogen water supplied to a vegetable compartment, for example. These hydrogen water using appliances also make use of the anti-oxidation effect of hydrogen.

When hydrogen is supplied to the house group 200 in the form of liquid hydrogen, the hydrogen using facility 214 may be an air conditioner or a refrigerator using the latent heat of liquid hydrogen. More specifically, liquid hydrogen absorbs a large amount of latent heat when it is vaporized. Using this latent heat allows cooling of a coolant in an air conditioner or a refrigerator. This achieves efficient use of the latent heat of liquid hydrogen.

As described above, the hydrogen using facility 214 is installable in various forms on the house 210 to allow use of hydrogen in various forms. Further, the provision of the facilities 212 and 214 that use hydrogen in the house group 200 allows contribution to carbon reduction through use of hydrogen.

Each house 210 in the house group 200 is connected to the hydrogen tank 220 provided to that house group 200 through a pipeline 240, and receives supply of hydrogen through the pipeline 240. The pipeline 240 connects the multiple house groups 200 to each other, and connects each house group 200 and the FC power generating facility 100 to each other. For electric power supply, each house group 200 and the FC power generating facility 100 are connected to each other through a power transmission line 260.

Hydrogen may pass through the pipeline 240 in various forms such as hydrogen gas, liquid hydrogen, methane produced from hydrogen gas, and methylcyclohexane (MCH). These types of gas or liquid all function as fuel containing hydrogen and will be called "hydrogen-containing fuel" accordingly. In this specification, the term "hydrogen" is also used as a term meaning the hydrogen-containing fuel. The pipeline 240 is generally feasible as piping for passage of the hydrogen-containing fuel. Using methane as the hydrogen-containing fuel allows piping for city gas to be used as the pipeline 240, making it possible to construct the pipeline 240 easily. While not shown in the drawings, the pipeline 240 is provided with various types of units prepared according to demand such as a valve, a pump, a compressor, a pressure accumulator, a converter for the hydrogen-containing fuel, a pressure gage, a thermometer, and a flow meter, for example.

The multiple solar panels 250 installed on the house group 200 include a power generating unit that generates electric power using sunlight, and a hydrogen producing unit that produces hydrogen via electrolysis of water using the electric power generated by the power generating unit. The electric power generated by the solar panels 250 may be consumed by electrical appliances in the house group 200, or may be accumulated in the secondary cell 230 in the house group 200 or the secondary cell 120 of the FC power generating facility 100. The hydrogen produced by the solar panels 250 may be consumed by the hydrogen using facility 214 in the house group 200, or may be stored in the hydrogen tank 220 in the house group 200.

As described above, two energy forms, electric power and hydrogen, are available as energy using hydrogen. Energy in the form of electric power is suitable for short-period keeping of the energy, and energy in the form of hydrogen is suitable for long-period keeping of the energy. The reason for this is as follows. Electric power is more easily available and thus more suitable for short-period keeping than hydrogen. Hydrogen has less loss during keeping and is thus more suitable for long-time keeping than electric power. The energy management system 400 preferably performs proper management on the keeping of energy in the form of electric power and in the form of hydrogen in consideration of such characteristics of electric power and hydrogen and in consideration of electric power demand and hydrogen demand.

The amount of electric power and the amount of hydrogen generated and produced by the multiple solar panels 250 in the house group 200 are allocated to the multiple houses 210 in that house group 200. For example, the amount of hydrogen produced by the multiple solar panels 250 in one house group 200 may be allocated uniformly to the multiple houses 210 belonging to that house group 200, or may be allocated in response to an area occupied by each house 210. The amount of produced hydrogen allocated to each house 210 increases hydrogen possession at that house 210. The amount of hydrogen used by the hydrogen using facility 214 or the hydrogen supply nozzle 212 in each house 210 reduces hydrogen possession at that house 210. The energy management system 400 is responsible for management of such hydrogen possession. Electric power generated by the solar panels 250 is managed in the same way. As described above, the provision of the hydrogen tank 220 and the solar panels 250 in the house group 200 makes the house group 200 itself available as a hydrogen buffer to allow efficiency increase in the use of hydrogen. This applies to electric power in the same way.

One hydrogen tank 220 as a hydrogen storage may be provided in one house group 200. In this case, hydrogen possession at each house 210 in that house group 200 is stored in one hydrogen tank 220 in that house group 200. By doing so, hydrogen possession at each house 210 in the house group 200 is to be stored in one hydrogen tank 220 in that house group 200, making it possible to manage hydrogen possession at each house 210 easily. Alternatively, one house group 200 may be provided with multiple hydrogen tanks 220 allocated to corresponding houses 210 in that house group 200, and hydrogen possession at each house 210 in that house group 200 may be stored in the hydrogen tank 220 allocated to that house 210. By doing so, hydrogen possession at each house 210 is to be stored in the hydrogen tank 220 allocated to that house 210, making it possible to manage hydrogen possession at each house 210 easily.

In the illustration of FIG. 1, the three existing house groups 200a to 200c are arranged around the FC power generating facility 100, and a planned site for the one house group 200d to be built additionally is reserved. Such arrangement of the multiple house groups 200a to 200d around the one FC power generating facility 100 allows sharing of the one FC power generating facility 100 among the multiple house groups 200a to 200d. This makes it possible to increase efficiency in the use of the FC power generating facility 100, while making it possible to increase efficiency in the use of hydrogen. In particular, locating the FC power generating facility 100 at a substantially central position among the multiple house groups 200a to 200d realizes an arrangement in which the FC power generating facility 100 is easily available for the multiple house groups 200a to 200d. Further, this arrangement allows an increase in equipment efficiency, compared to an arrangement in which the FC power generating facility 100 is provided for each house group 200. The arrangement of the FC power generating facility 100 and the multiple house groups 200 will be described again in detail in a different embodiment described later.

The hydrogen station 300 includes a hydrogen tank 320 as a hydrogen storage, and a hydrogen dispenser 310 for filling the fuel cell vehicle FCV with hydrogen. The hydrogen tank 320 is connected through the pipeline 240 to the multiple house groups 200, to the factory 500 with a hydrogen producing device 510, and to the ammonia-hydrogen converting facility 600. The hydrogen dispenser 310 is one type of hydrogen filler for filling the fuel cell vehicle FCV with hydrogen.

The fuel cell vehicle FCV is preferably a large-sized vehicle such as a bus located in the community. The large-sized fuel cell vehicle FCV includes a hydrogen tank of a large capacity and produces a large output from a fuel cell, and is hence used effectively as a hydrogen source or a power source at a time of disaster. In order to function as a power supply, the fuel cell vehicle FCV is preferably provided with an external power feeder for supplying electric power to the outside. The fuel cell vehicle FCV is particularly preferably located at a public installation such as a public office, a hospital, or a school in the community. This makes it possible to offer a hydrogen source or a power source promptly to the public installation at the time of disaster.

The energy management system 400 has the function of managing hydrogen and electric power in the community system shown in FIG. 1. For management of hydrogen and electric power, the energy management system 400 communicates with the other facilities 100, 200, 300, 500, and 600 in the community system. In the illustration of FIG. 1, the communication between the energy management system 400 and the other facilities 100, 200, 300, 500, and 600 is radio communication. Alternatively, the communication may be made through wires partially or entirely. An example of management of hydrogen and electric power by the energy management system 400 will be described in more detail later. Electric power may be managed by a different system.

The factory 500 includes the hydrogen producing device 510, and a hydrogen tank 520 as a hydrogen storage. The hydrogen producing device 510 is a device that produces hydrogen using waste heat in the factory 500, for example. Alternatively, the hydrogen producing device 510 may be configured as a device that separates hydrogen from by-product gas produced through a steelmaking process or a chemical process performed in the factory 500. The hydrogen tank 520 in the factory 500 is connected to the pipeline 240. Making the hydrogen producing device 510 produce hydrogen using waste heat in the factory 500 and using the produced hydrogen in the community system allows effective use of the waste heat in the factory 500, making it possible to increase efficiency in the use of hydrogen and energy in the community system. This similarly applies to the case of using hydrogen in by-product gases from the factory 500.

A process of producing hydrogen in the factory 500 to be used in the community may be performed in a shutdown period of the factory 500. This allows efficient use of waste heat or by-product hydrogen in the shut-down period of the factory 500. Hydrogen may be produced in this way not only in the factory 500 but also in a different commercial and industrial installation. The "commercial and industrial installation" mentioned herein has a wide meaning covering a commercial installation and an industrial installation. The hydrogen producing device 510 in the factory 500 corresponds to a hydrogen producing device that produces hydrogen using waste heat generated in a commercial and industrial installation or produces hydrogen from by-product gas produced in the commercial and industrial installation. Using the hydrogen producing device 510 in this way allows effective use of waste heat or by-product gas in the commercial and industrial installation, making it possible to increase efficiency in the use of hydrogen and energy in the community system.

The ammonia-hydrogen converting facility 600 includes an ammonia tank 610, a hydrogen tank 620, and an ammonia-hydrogen converter 630. The ammonia tank 610 stores ammonia supplied from an ammonia transport vessel ATV staying at a harbor PT, for example. The ammonia transport vessel ATV transports ammonia imported from a foreign country, for example, to the harbor PT. Ammonia may be transported from the ammonia transport vessel ATV to the ammonia tank 610 using a tank truck. However, using a pipeline achieves the transport more easily. If the tank truck is used for transporting ammonia, the ammonia-hydrogen converting facility 600 is not required to be arranged at the harbor PT. Meanwhile, due to the strongly irritating odor of ammonia, the ammonia-hydrogen converting facility 600 is preferably arranged away from the house group 200 as much as possible.

The decomposition of ammonia in an ammonia-hydrogen converting process requires a heat source as it is an endothermic reaction. Thus, heat resulting from combustion of ammonia is generally used as the heat source. Alternatively, waste heat from the factory 500 may be used as the heat source in the ammonia-hydrogen converting process. In this case, piping for carrying a waste heat supply medium is preferably placed between the factory 500 and the ammonia-hydrogen converting facility 600, because it allows production of hydrogen through the effective use of the waste heat in the community system.

Hydrogen produced by the ammonia-hydrogen converter 630 is accumulated in the hydrogen tank 620. The hydrogen tank 620 is connected to the pipeline 240. In other words, hydrogen produced by the ammonia-hydrogen converter 630 is supplied to other facilities in the community system through the pipeline 240.

The ammonia-hydrogen converter 630 may supply the pipeline 240 with a mixed gas of hydrogen including ammonia. Generally, ammonia of a certain amount is left after the ammonia decomposing process performed by the ammonia-hydrogen converter 630. In this regard, to increase the purity of hydrogen, an ammonia removing process is generally performed after the ammonia decomposing process. In this ammonia removing process, adjusting a process parameter so as to leave a tiny amount of ammonia unremoved allows for preparation of the mixed gas containing the tiny amount of ammonia mixed into hydrogen. This mixed gas is prepared by a simple method of controlling the ammonia removing process performed by the ammonia-hydrogen converter 630, making it possible to prepare the hydrogen-ammonia mixed gas easily. In preparation for supply of the hydrogen-ammonia mixed gas through the pipeline 240, ammonia is preferably removed from the mixed gas with an ammonia filter, for example, before a hydrogen using facility in the community system uses hydrogen supplied through the pipeline 240.

An ammonia concentration in the mixed gas is preferably set in a range of 2 ppm or more and 100 ppm or less, for example, and preferably in a range of 2 ppm or more and 50 ppm or less. The ammonia concentration of 2 ppm is at a level at which the odor of ammonia is detectable sufficiently and easily by a human. The ammonia concentration of 50 ppm is at a level at which the odor of ammonia is emitted strongly. The ammonia concentration of 100 ppm is at a level at which the odor of ammonia is emitted more strongly but the toxicity of ammonia does not cause an excessively adverse effect to a human body. In consideration of these, setting a lower limit of the ammonia concentration at 2 ppm makes the odor of ammonia detectable by a human in the case of leakage of the mixed gas, thereby facilitating detection of leakage of the mixed gas. Setting an upper limit of the ammonia concentration at 100 ppm may cause emission of a strong odor of ammonia in the case of leakage of the mixed gas. However, ammonia at this concentration is not so high as to cause an excessively adverse effect to a human body due to the toxicity of ammonia. To emit the odor of ammonia sufficiently while the ammonia concentration is controlled at a sufficiently low level, the ammonia concentration is still preferably set in a range of 2 ppm or more and 50 ppm or less.

Figure 2:
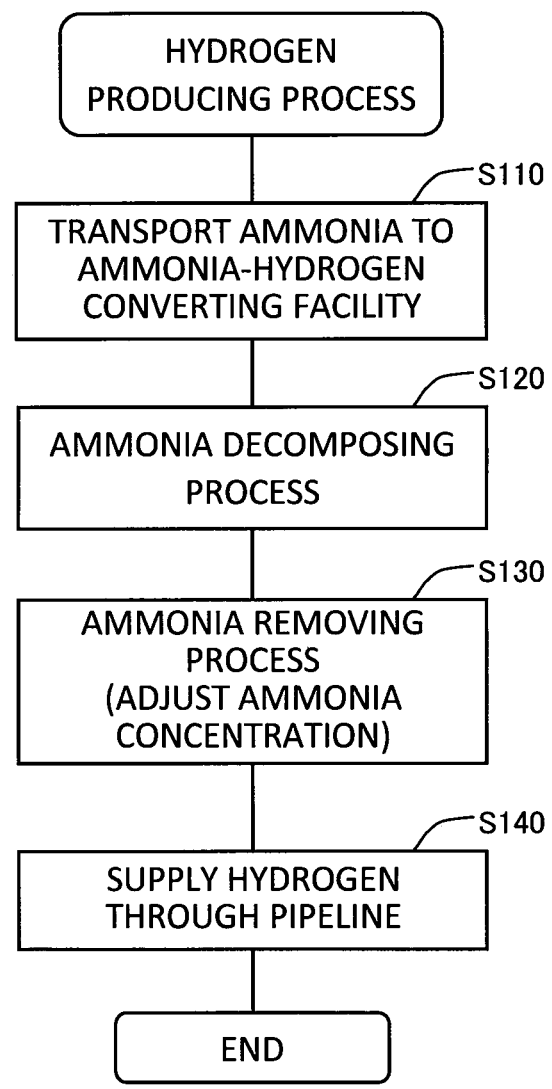
FIG. 2 is a flowchart showing a procedure of a hydrogen production method employed in an ammonia-hydrogen converting facility.

FIG. 2 is a flowchart showing a procedure of a hydrogen production method employed in the ammonia-hydrogen converting facility 600. First, in step S110, ammonia is transported to the ammonia-hydrogen converting facility 600. The ammonia may be transported using a tank truck or through a pipeline. In step S120, the ammonia-hydrogen converter 630 performs the ammonia decomposing process to produce hydrogen. In step S130, the ammonia-hydrogen converter 630 performs the ammonia removing process. In this process, an ammonia concentration may be set in the foregoing preferable range. In step S140, the produced hydrogen or mixed gas is supplied to a different facility in the community system through the pipeline 240. According to this hydrogen production method, hydrogen is produced from ammonia in the industrial area IA suitable for handling ammonia and the produced hydrogen is available in the community system.

In FIG. 1, facilities provided as the hydrogen source include the solar panels 250 installed on the house group 200, the hydrogen producing device 510 in the factory 500, and the ammonia-hydrogen converter 630. The community system may include only one of these hydrogen sources. Facilities provided as the hydrogen storage include the hydrogen tank 220 in the house group 200, the hydrogen tank 320 in the hydrogen station 300, the hydrogen tank 520 in the factory 500, and the hydrogen tank 620 in the ammonia-hydrogen converting facility 600. The community system may include only one hydrogen storage. The pipeline 240 may be configured to be used for supplying hydrogen from at least one of the hydrogen source and the hydrogen storage to the FC power generating facility 100, the hydrogen station 300, and the house group 200.

As described above, the community system shown in FIG. 1 includes the hydrogen source such as the solar panels 250, the hydrogen storage such as the hydrogen tank 220, and various types of facilities that use hydrogen. Further, the energy management system 400 manages hydrogen in the community system. This enables hydrogen to be used smoothly to encourage higher efficiency in the use of hydrogen. In particular, connecting these facilities to each other through the pipeline 240 allows efficiency increase in the use of hydrogen to a greater extent. Additionally, the provision of the solar panels 250 for production of hydrogen using sunlight and the hydrogen tank 220 as the hydrogen storage in the house group 200 allows the house group 200 to function as a hydrogen buffer in which hydrogen is accumulated or from which hydrogen is released in response to a status of use of hydrogen.

Figure 3:
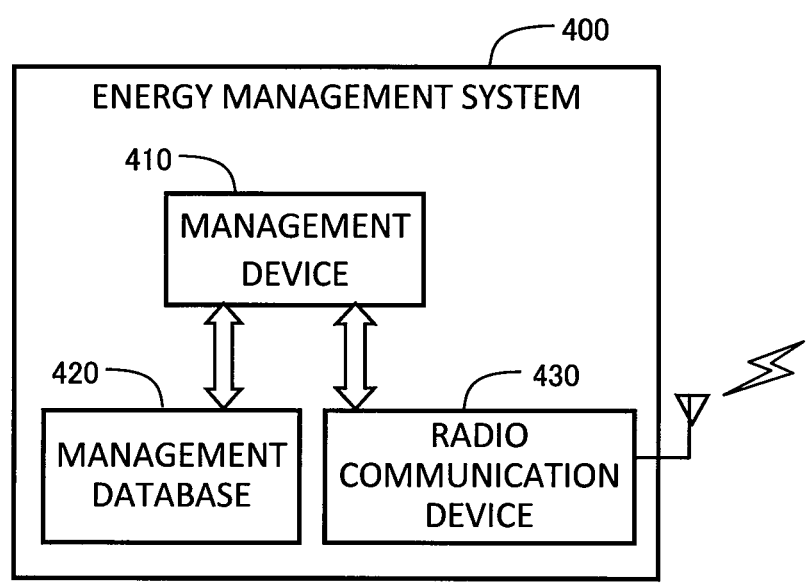
FIG. 3 is a functional block diagram showing a function of an energy management system.

FIG. 3 is a functional block diagram showing the function of the energy management system 400. The energy management system 400 includes a management device 410, a management database 420, and a radio communication device 430. The management device 410 is realized by a computer including a processor and a memory, for example. The management database 420 is a database for management of hydrogen and electric power in the community system. The radio communication device 430 performs radio communications with a different facility in the community system to receive energy balance information including the amount of used hydrogen and the amount of used electric power, and the amount of produced hydrogen and the amount of produced electric power at each facility. The management device 410 updates the management database 420 using the received energy balance information to manage hydrogen and electric power.

FIG. 4 is an explanatory view showing an example of a hydrogen management database HMD registered in the management database 420. Multiple records are registered in the hydrogen management database HMD. One record contains a house ID, a current hydrogen residual amount V1, a last-month-end hydrogen residual amount V2, a hydrogen production amount V3, a hydrogen consumption amount V4, a hydrogen purchase amount V5, and a hydrogen sale amount V6. The house ID is an ID for identifying each house 210 in the house group 200.

The pieces of information V1 to V6 about hydrogen amounts are related to each other as follows:

$$V1=V2+V3+V4+V5+V6 \tag{1}$$

The pieces of information V1 to V6 about hydrogen amounts have the following meanings:

(1) Current hydrogen residual amount V1

The current hydrogen residual amount V1 is hydrogen possession at a corresponding house 210 at the present time.

(2) Last-month-end hydrogen residual amount V2

The last-month-end hydrogen residual amount V2 is hydrogen possession at the corresponding house 210 at the end of the last month.

(3) Hydrogen production amount V3

The hydrogen production amount V3 is an increase in hydrogen possession at the corresponding house 210 in a period from the beginning of the current month to the present time. For example, the hydrogen production amount V3 is an amount allocated to the corresponding house 210 out of the amount of hydrogen produced by the solar panels 250 as a hydrogen producing device in the house group 200 including the corresponding house 210. In each house group 200, allocation information indicating a way of allocating the amount of hydrogen produced by the solar panels 250 in that house group 200 to each house 210 is set in advance in the management database 420.

(4) Hydrogen consumption amount V4

The hydrogen consumption amount V4 is the amount of hydrogen consumed by the corresponding house 210 in the period from the beginning of the current month to the present time. The hydrogen consumption amount V4 is the sum of the amount of hydrogen consumed through the hydrogen supply nozzle 212 and the amount of hydrogen consumed by the hydrogen using facility 214 at the corresponding house 210.

(5) Hydrogen purchase amount V5

The hydrogen purchase amount V5 is the amount of hydrogen purchased from the outside by the corresponding house 210 in the period from the beginning of the current month to the present time.

(6) Hydrogen sale amount V6

The hydrogen sale amount V6 is the amount of hydrogen sold to the outside by the corresponding house 210 in the period from the beginning of the current month to the present time. A difference between the hydrogen sale amount V6 and the hydrogen purchase amount V5 (V6−V5) corresponds to a hydrogen transfer amount transferred from each house 210.

Each house 210 may purchase or sell hydrogen using a management device provided at each house 210, or using an application program installed by a resident of each house 210 on a smartphone or a personal computer.

The energy management system 400 updates the current hydrogen residual amount V1 corresponding to hydrogen possession at each house 210 using the amount of produced hydrogen or consumed hydrogen, thereby allowing management of increase or decrease in hydrogen at each house 210. The energy management system 400 reflects, in the current hydrogen residual amount V1 corresponding to hydrogen possession at each house 210, a hydrogen transfer amount (V6−V5) transferred from the same house 210, making it possible to facilitate use of hydrogen at each house 210 to a greater extent. When hydrogen is transferred from one house 210, hydrogen of the amount of the transfer (V6−V5) may actually be moved to the hydrogen tank 220 provided in the house group 200 including that house 210, or only a hydrogen ownership may be handed over without actually moving hydrogen. Each of these ways allows efficient use of hydrogen in the community system.

Figure 5:
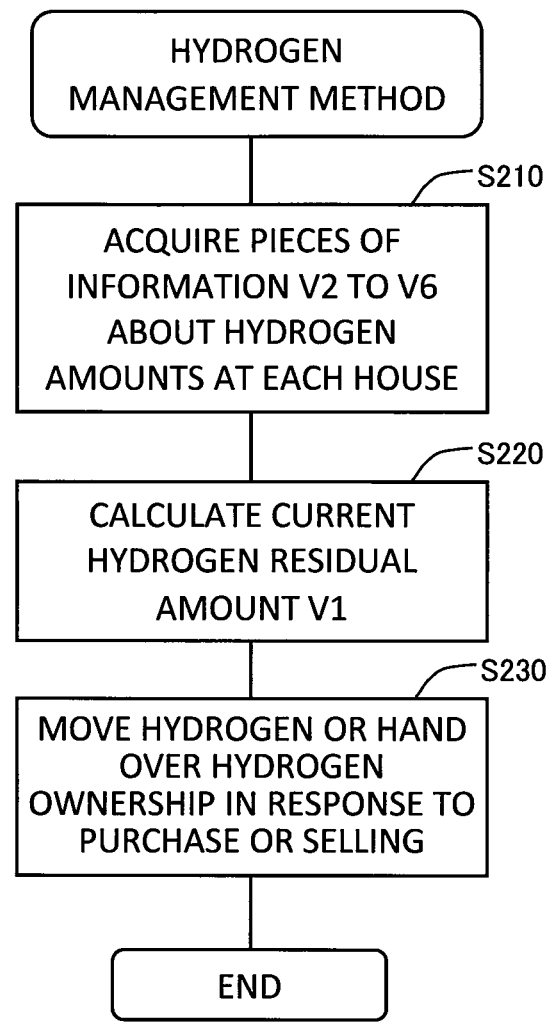
FIG. 5 is a flowchart showing a procedure of a hydrogen management method employed in the community system.

FIG. 5 is a flowchart showing a procedure of a hydrogen management method performed in the energy management system 400. The procedure in FIG. 5 is performed repeatedly at certain time intervals, for example. In step S210, the management device 410 acquires the pieces of information V2 to V6 about hydrogen amounts at each house 210. Some of these pieces of information V2 to V6 about hydrogen amounts may be acquired by being read from the management database 420. The other of the pieces of information V2 to V6 about hydrogen amounts may be acquired from a management device provided at each house 210. In step S220, the management device 410 calculates the current hydrogen residual amount V1 from the acquired pieces of information V2 to V6 about hydrogen amounts. Further, the management device 410 updates the management database 420 using these pieces of information V1 to V6 about hydrogen amounts. In step S230, in response to the hydrogen purchase amount V5 or the hydrogen sale amount. V6 corresponding to a hydrogen transfer amount, hydrogen is actually moved to the hydrogen tank 220, or only a hydrogen ownership is handed over without actually moving hydrogen. According to this hydrogen management method, the amount of hydrogen transfer from each house 210 is reflected in hydrogen possession at the same house 210, making it possible to facilitate use of hydrogen at each house 210 to a greater extent.

A hydrogen amount may be managed in a similar way to that shown in FIGS. 4 and 5 not only for the house 210 but also for a different facility that performs at least one of the production and consumption of hydrogen. More specifically, the energy management system 400 may manage a hydrogen amount for the FC power generating facility 100, the hydrogen station 300, the factory 500, and the ammonia-hydrogen converting facility 600, for example. Further, the energy management system 400 may manage not only a hydrogen amount but also an electric power amount in a similar way to that shown in FIGS. 4 and 5 for the house 210 or each facility.

As described above, the energy management system 400 adjusts production and consumption of hydrogen and electric power in the community system, thereby allowing hydrogen and electric power to be used smoothly, allowing efficiency increase in the use of hydrogen and electric power, and allowing contribution to carbon reduction. Further, the provision of the solar panels 250 as a hydrogen producing device and the hydrogen tank 220 in the house group 200 itself allows the house group 200 to function as a buffer for hydrogen and electricity.

Figure 6:
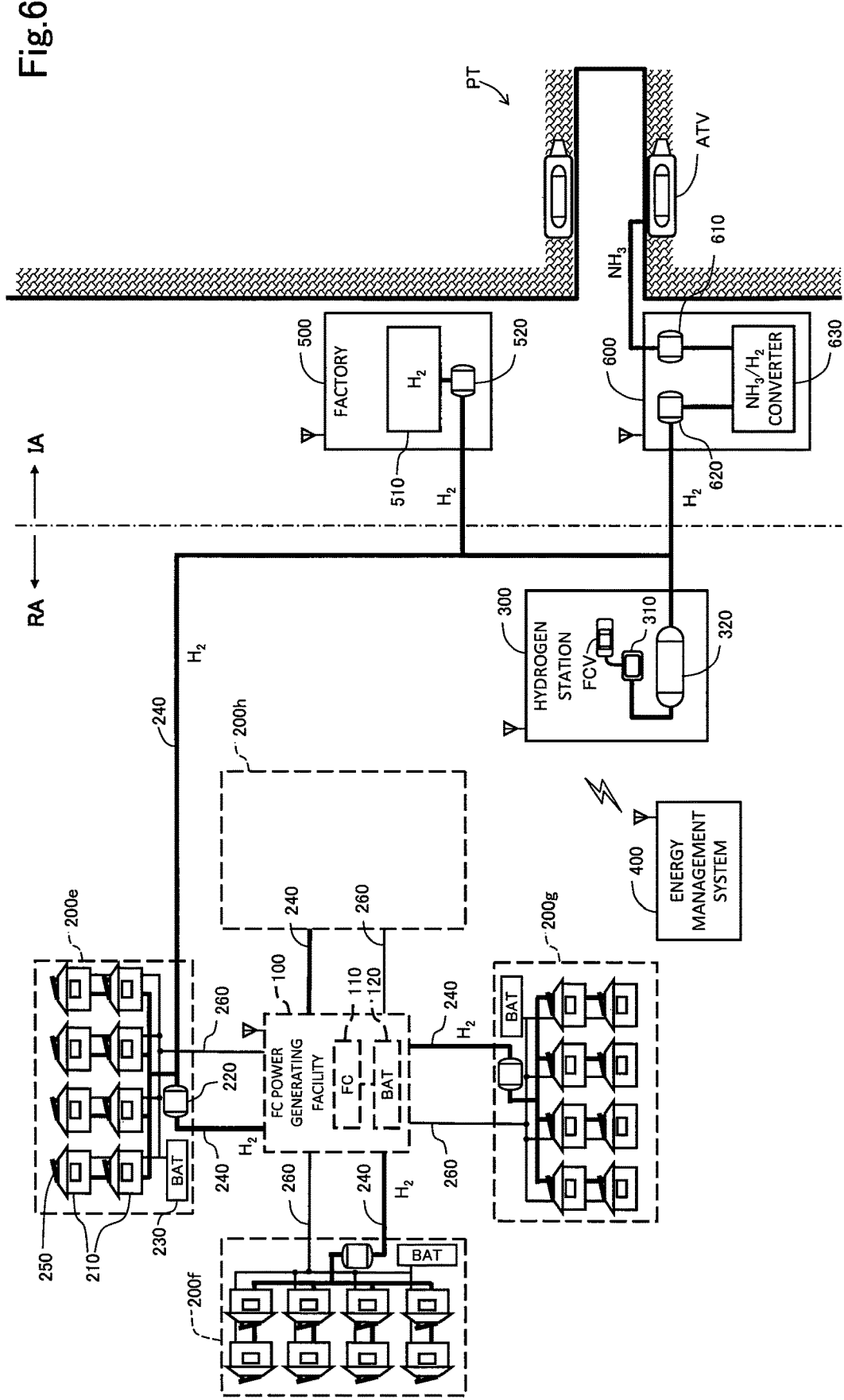
FIG. 6 is an explanatory view showing the configuration of a community system according to a different embodiment.

FIG. 6 is an explanatory view showing the configuration of a community system according to a different embodiment. This community system differs from that shown in FIG. 1 only in the following two points. The configuration of the community system of FIG. 6 is the same in other respects as that of FIG. 1.

(1) The house groups 200a to 200d in the community system of FIG. 1 are changed to a house group 200e, a house group 200f, a house group 200g, and a house group 200h.

(2) The FC power generating facility 100 is buried underground.

Each of the house groups 200e to 200h in FIG. 6 is not a housing complex but is a group of detached houses 210. At least some of the multiple houses 210 forming each house group 200 are provided with the solar panels 250. While not shown in the drawings, at least some of the multiple houses 210 may be provided with the hydrogen using facility 214 or the hydrogen supply nozzle 212 described by referring to FIG. 1. Like in the community system of FIG. 1, each house group 200 is provided with the hydrogen tank 220 and the secondary cell 230. The community system shown in FIG. 6 has substantially the same configuration and achieves substantially the same effect as the community system shown in FIG. 1.

In the community system of FIG. 6, the FC power generating facility 100 is buried underground. A land surface above the FC power generating facility 100 is available as a facility for residents of the multiple house groups 200 such as a playground, an assembly hall, or a parking lot. In this case, the pipeline 240 and the power transmission line 260 are also preferably buried underground. Regarding a planned site for the house group 200h to be additionally built, the pipeline 240 and the power transmission line 260 for connecting the house group 200h and the FC power generating facility 100 are preferably buried underground in advance, or underground conduits are preferably prepared for routing of the pipeline 240 and the power transmission line 260.

In the community system shown in FIG. 6, the FC power generating facility 100 is located at a position facing all the multiple house groups 200e to 200h. In other words, the FC power generating facility 100 is located at a position facing all the plurality of house groups 200e to 200g, or a position facing all the plurality of house groups 200e to 200g and the planned site where the new house group 200h is to be built. This achieves an arrangement in which the FC power generating facility 100 is easily available for the multiple house groups 200e to 200h. This arrangement further allows an increase in equipment efficiency, compared to an arrangement in which the FC power generating facility 100 is provided for each house group 200. The FC power generating facility 100 is still preferably located at a substantially central position among the multiple existing house groups 200e to 200g, or a substantially central position among the multiple existing house groups 200e to 200g and the planned site where the new house group 200h is to be built. By doing so, the FC power generating facility 100 becomes more easily available for the multiple house groups 200e to 200h. "Locating the FC power generating facility 100 at a substantially central position among the multiple existing house groups 200e to 200g" means that, assuming that an average of distances from the multiple house group 200e to 200g to the FC power generating facility 100 is 100%, a distance from each house group 200 to the FC power generating facility 100 is within a range of 100% plus or minus 20%. A distance from one existing house group 200 to the FC power generating facility 100 means the shortest distance in a plan view from one house 210 among the multiple houses 210 belonging to that house group 200 and nearest the FC power generating facility 100, up to the FC power generating facility 100. A distance from the planned site where the new house group 200h is to be built to the FC power generating facility 100 means the shortest distance in a plan view from a circumscribed rectangle on that planned site to the FC power generating facility 100. These features and preferable configurations also apply to the community system of FIG. 1.

Figure 7:
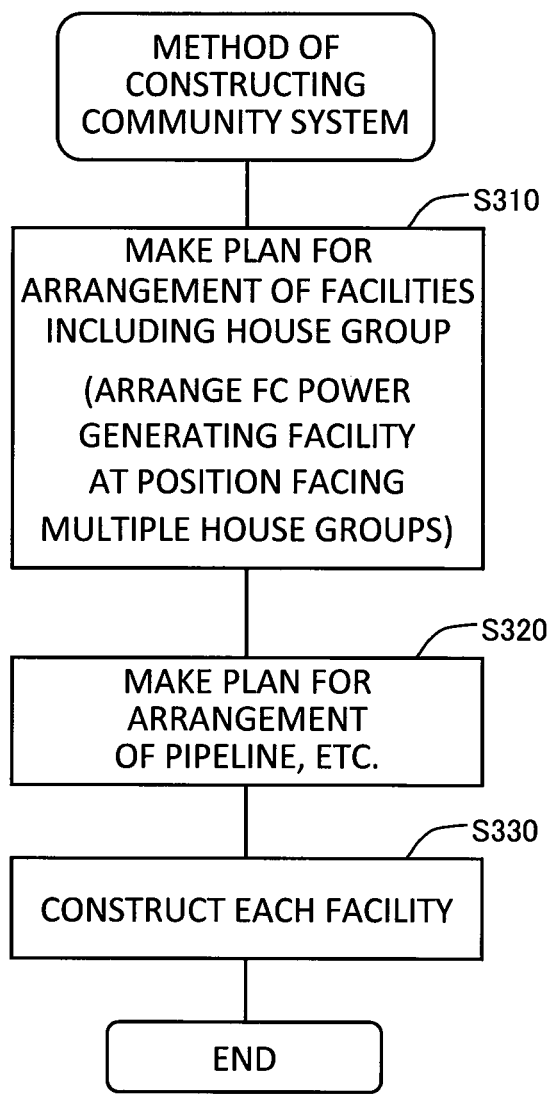
FIG. 7 is a flowchart showing a procedure of a construction method of constructing the community system.

FIG. 7 is a flowchart showing a procedure of a construction method of constructing the community system. In step S310, a plan is made for the arrangement of facilities in the community system including the house groups 200, the FC power generating facility 100, the hydrogen station 300, the energy management system 400, etc. In this step, as has been described by referring to FIG. 6, the FC power generating facility 100 is preferably located at a position facing all the multiple house groups 200e to 200h. This also applies to the illustration of FIG. 1, so that the FC power generating facility 100 is preferably located at a position facing all the multiple house groups 200a to 200d. In step S320, a plan is made for the arrangement of the pipeline 240, the power transmission line 260, etc. In step S330, each facility is built by following the arrangement plans made in steps S310 and S320. According to this construction method, the FC power generating facility 100 is located at a position facing all the multiple house groups 200, so that the resultant arrangement makes the FC power generating facility 100 easily available for the multiple house groups 200. Further, this arrangement allows an increase in equipment efficiency, compared to an arrangement in which the FC power generating facility 100 is provided for each house group 200.

The community system according to each of the foregoing embodiments includes the FC power generating facility 100, the house group 200, the hydrogen filler such as the hydrogen station 300, the energy management system 400, and the facilities 500 and 600 each including the hydrogen producing device. This allows construction of a local system achieving efficient use of hydrogen and electric power by means of relatively small investment on an area to cover the community system. As a result, the value of this community system as a brand rises to bring a significant advantage to that area and residents in that area. Further, this community system uses hydrogen and solar energy as main energy sources, making it possible to provide $CO_2$-free life to the residents. Each house 210 in the house group 200 is provided with the fuel cell vehicle FCV as a standard facility, making it possible to provide the residents with $CO_2$-free mobility. Meanwhile, some of the installations or facilities described in each of the embodiments are omissible.

(1) According to one aspect of the present disclosure, a community system that uses hydrogen is provided. The community system comprises: a hydrogen source; a hydrogen storage storing hydrogen supplied from the hydrogen source; an FC power generating facility with a fuel cell that generates electric power using hydrogen supplied from at least one of the hydrogen source and the hydrogen storage; a hydrogen filler that fills a fuel cell vehicle with hydrogen supplied from at least one of the hydrogen source and the hydrogen storage; a house group with multiple houses that use electric power supplied from the FC power generating facility and hydrogen supplied from at least one of the hydrogen source and the hydrogen storage; and a management system that manages hydrogen in the community system. The hydrogen source is a hydrogen producing device that produces hydrogen using waste heat generated in a commercial and industrial installation or produces hydrogen from by-product gas produced in the commercial and industrial installation.

This community system includes the hydrogen source, the hydrogen storage, and various types of facilities that use hydrogen. Further, the management system manages hydrogen in the community system. This enables hydrogen to be used smoothly to encourage higher efficiency in the use of hydrogen. Additionally, because the hydrogen source is the hydrogen producing device that produces hydrogen from waste heat or by-product gas produced in the commercial and industrial installation, the waste heat or by-product gas in the commercial and industrial installation is used effectively, making it possible to increase efficiency in the use of hydrogen and energy in the community system.

(2) In the foregoing community system, the hydrogen source may produce hydrogen in a shutdown period of the commercial and industrial installation.

In this community system, because hydrogen is produced in the shutdown period of the commercial and industrial installation, it becomes possible to efficiently use waste heat or by-product hydrogen produced in the shut-down period.

The present disclosure is feasible in various aspects such as a community system, a management device and a management method for managing the community system, a construction method of constructing the community system, and a hydrogen production method employed in the community system, for example.

The disclosure is not limited to any of the embodiment and its modifications described above but may be implemented by a diversity of configurations without departing from the scope of the disclosure. For example, the technical features of any of the above embodiments and their modifications may be replaced or combined appropriately, in order to solve part or all of the problems described above or in order to achieve part or all of the advantageous effects described above. Any of the technical features may be omitted appropriately unless the technical feature is described as essential in the description hereof. The present disclosure may be implemented by aspects described below.

What is claimed is:
1. A community system that uses hydrogen, comprising:
a hydrogen source;
a hydrogen storage storing hydrogen supplied from the hydrogen source;

an FC power generating facility with a fuel cell that generates electric power using hydrogen supplied from at least one of the hydrogen source and the hydrogen storage;
a hydrogen filler that fills a fuel cell vehicle with hydrogen supplied from at least one of the hydrogen source and the hydrogen storage;
a house group with multiple houses that use electric power supplied from the FC power generating facility and hydrogen supplied from at least one of the hydrogen source and the hydrogen storage; and
a management system that manages hydrogen in the community system, wherein
the hydrogen source is a hydrogen producing device that produces hydrogen using waste heat generated in a commercial and industrial installation or produces hydrogen from by-product gas produced in the commercial and industrial installation.

2. The community system according to claim 1, wherein the hydrogen source produces hydrogen in a shutdown period of the commercial and industrial installation.

* * * * *